United States Patent
Ramin et al.

(10) Patent No.: US 6,296,839 B1
(45) Date of Patent: Oct. 2, 2001

(54) NAIL VARNISH WITH A CHASED EFFECT

(75) Inventors: Roland Ramin, Paris; Ingrid Brenne, L'Hay-les-Roses, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/538,978

(22) Filed: Mar. 30, 2000

(30) Foreign Application Priority Data

Mar. 31, 1999 (FR) .................................. 99 04047

(51) Int. Cl.⁷ .............................. A61K 7/04; A61K 7/00
(52) U.S. Cl. .............................. 424/61; 424/401
(58) Field of Search ....................... 424/61, 401

(56) References Cited

U.S. PATENT DOCUMENTS

| | | |
|---|---|---|
| 2,884,388 * | 4/1959 | Hedlund . |
| 4,158,053 | 6/1979 | Greene et al. . |
| 4,822,423 | 4/1989 | Soyama et al. . |
| 5,833,967 | 11/1998 | Ramin . |
| 5,882,635 | 3/1999 | Ramin et al. . |
| 5,910,313 | 6/1999 | Ramin et al. . |
| 5,965,111 * | 10/1999 | Ellingson et al. ............... 424/61 |
| 6,099,826 * | 8/2000 | Ramin ............................... 424/61 |

FOREIGN PATENT DOCUMENTS

| | | |
|---|---|---|
| 0 705 594 | 4/1996 | (EP) . |
| 0 745 372 | 12/1996 | (EP) . |
| 0 797 977 | 10/1997 | (EP) . |
| 0 819420 | 1/1998 | (EP) . |
| 2 578 741 | 9/1986 | (FR) . |
| 2 021 411 | 12/1979 | (GB) . |

OTHER PUBLICATIONS

Derwent Publications Ltd., London, GB; AN 1996–438259, XP002126526 (JP 08 216331).
English language Derwent Abstract of EP 0 705 594.

* cited by examiner

Primary Examiner—Thurman K. Page
Assistant Examiner—Blessing Fubara
(74) Attorney, Agent, or Firm—Finnegan, Henderson, Farabow, Garrett, & Dunner, L.L.P.

(57) ABSTRACT

A nail varnish composition containing, in an organic solvent medium, at least one film-forming polymer, at least one metal pigment, at least one organopolysiloxane and at least one pyrogenic silica. A make-up kit containing a first composition containing at least one first film-forming polymer and a second composition containing, in an organic solvent medium, at least one second film-forming polymer, at least one metal pigment, at least one organopolysiloxane and at least one pyrogenic silica. A process for making up nails. The make-up obtained exhibits a chased appearance.

86 Claims, No Drawings

NAIL VARNISH WITH A CHASED EFFECT

The present invention is directed to a nail varnish composition comprising, in an organic solvent medium, a film-forming polymer, pyrogenic silica, a metal pigment, and an organopolysiloxane. The invention is also directed to a process for making up the nails, in particular the nails of human beings, or false nails.

Nail varnish compositions generally comprise a film-forming polymer, either dissolved in an organic solvent or dispersed in the form of particles in an aqueous medium, and a colouring material, in particular a pigment. Such varnishes are disclosed, for example, in U.S. Pat. No. 4,158,053 and French Patent Application No. A-2,578,741, the disclosures of both of which are hereby incorporated by reference.

After the application to the nail of one or more layers and then drying, these nail varnishes generally result in the formation of a smooth, continuous and homogeneous film which is glossy or matte. Some of the films obtained also exhibit good cosmetic properties, such as good hold and, in particular, good adhesion to the nail and good resistance to water, to rubbing movements, and to impacts.

With changing fashion, consumers, who are increasingly demanding, are looking for novel make-up products which confer original or specific make-up effects. A need therefore remains to have available a make-up product which, when applied to a substrate, such as human nails, skin or hair, results in a make-up effect different from those of the smooth, continuous and homogeneous films currently obtained with the commercially available products.

Furthermore, a surface coating composition which produces a film with a chased appearance on the substrate where it is applied, such as a metal surface or a surface of wood or paper, is known from U.S. Pat. No. 2,884,388, the disclosure of which is hereby incorporated by reference. The chased appearance corresponds to the aggregation of metal pigment at the surface of the film in the form of small protuberant circles which are evenly distributed and exhibit the appearance of craters. This appearance is obtained with a composition comprising, in an organic solvent medium, a film-forming polymer, a metal pigment and a specific silicone compound. The composition is applied by vaporization in the form of a spray in order to obtain the desired chased effect.

Known nail varnish compositions are usually applied using a brush and exhibit a degree of consistency (in particular of thixotropy) in order to facilitate the application and to ensure good dispersion of the colored pigments in the medium. Thus, the use of clays, such as organo-modified montmorillonites, in order to obtain a varnish of the desired consistency, is known from the published Great Britain Patent Application No. GB-A-2,021,411.

On using the silicone compound and the metal pigment, according to U.S. Pat. No. 2,884,388, in a nail varnish composition comprising montmorillonite as the sole consistency agent, the Inventors have found that the film obtained, after application to the nails, does not exhibit a chased appearance. The film remains smooth and continuous, as for a conventional nail varnish.

The aim of the present invention is to provide a fluid nail varnish composition which is easy to apply and which results, after application, in a very even chased appearance which is highly visible to the eye.

The inventors have discovered, surprisingly, that a novel type of make-up for the nails can be obtained by using a film-forming composition comprising pyrogenic silica, a metal pigment, and a specific silicone compound.

More specifically, an embodiment of the present invention is a nail varnish composition comprising, in an organic solvent medium, at least one film-forming polymer, at least one pyrogenic silica, at least one metal pigment, and at least one specific organopolysiloxane.

Another embodiment of the invention is a process for making up the nails which comprises applying, to the nails, the composition as defined above.

When the composition is applied to the nails, craters are formed at the surface of the film during the drying, resulting in the migration of the metal pigment to the edges of the craters. The craters can be of different sizes and can have a more or less regular appearance, in particular in the form of a circle or ovoid. The craters can exhibit a gentle relief or else a sloping relief similar to a cone. The tip of the cone can be open and can allow the substrate to which the composition is applied to appear. After complete drying, the film exhibits a chased appearance.

The pyrogenic silica present in the composition, in addition to its role of consistency agent and rheological agent, is not harmful to the formation of the chased appearance, in contrast to montmorillonite used alone. An original make-up is thus obtained which can exhibit both good hold, in particular to rubbing movements and to chipping, and good adhesion to the nail.

This composition can advantageously be applied as the surface product, commonly known as a top coat.

Another embodiment of the invention is a cosmetic process for making up the nails which comprises applying, to the nails, a composition as defined above.

Another embodiment of the invention is a cosmetic process for making up the nails which comprises applying, to the nails, a first layer, also known as a base layer, of a first cosmetic composition comprising, in a cosmetically acceptable medium, a first film-forming polymer and then applying, to at least part of the first layer, a second layer, also known as a surface layer, of a second cosmetic composition comprising, in an organic solvent medium, at least one second film-forming polymer, at least one metal pigment and at least one organopolysiloxane, wherein the first composition does not comprise an organopolysiloxane that is the same as the at least one organopolysiloxane in the second composition.

Another embodiment of the invention is a make-up kit comprising:
  a first cosmetic composition (base layer composition) comprising, in a cosmetically acceptable medium, at least one first film-forming polymer;
  a second cosmetic composition (surface layer composition) comprising, in an organic solvent medium, at least one second film-forming polymer, at least one pyrogenic silica, at least one metal pigment and at least one organopolysiloxane, wherein the first composition does not comprise an organopolysiloxane that is the same as the at least one organopolysiloxane in the second composition.

A further embodiment of the invention is made-up false nails comprising a make-up which is capable of being obtained according to the process as defined above.

The organopolysiloxane present in the surface composition has a viscosity such that a 10% solution of organopolysiloxane in xylene has a viscosity at 25° C. ranging from 0.0002 $m^2/s$ to 0.01 $m^2/s$ (20 to 1000 centistokes), preferably from 0.0005 $m^2/s$ to 0.005 $m^2/s$ (50 to 500 centistokes) and better still from 0.001 $m^2/s$ to 0.0015 $m^2/s$ (100 to 150 centistokes). The viscosity is measured according to ASTM Standard D-445 with a glass capillary tube.

The organopolysiloxane has on average from 1.99 to 2.01 hydrocarbonaceous radicals per silicon atom. At least 50% of the units of the organopolysiloxane are units of formula RMeSiO in which R is an aliphatic radical having from 1 to 3 carbon atoms, the other remaining units being units of formula $R'_n SiO_{(2-n/2)}$ in which n has a mean value ranging from 1 to 3 and R' is a monovalent hydrocarbonaceous radical. In the composition according to the invention, the silica/film-forming polymer ratio by weight is other than 0.0116.

R can in particular be chosen from a methyl, ethyl, propyl, vinyl, and allyl radical. The organopolysiloxane can be chosen from polydimethylsiloxanes, polyethylmethylsiloxanes, polymethylvinylsiloxanes, polymethylpropylsiloxanes, polymethylallylsiloxanes, phenylmethylpolysiloxanes and their copolymers.

The monovalent hydrocarbonaceous radical R' can in particular be chosen from a ($C_1$–$C_{18}$) alkyl radical and in particular a methyl, ethyl, propyl and octadecyl radical; a ($C_1$–$C_6$) alkenyl radical, in particular vinyl, allyl or hexenyl; a ($C_6$–$C_{12}$) cycloaliphatic hydrocarbonaceous radical, in particular a cyclohexyl or cyclohexenyl radical; a ($C_7$–$C_{15}$) aralkyl hydrocarbonaceous radical, in particular a benzyl radical; and a ($C_6$–$C_{20}$) hydrocarbonaceous aromatic radical, in particular phenyl, tolyl, xenyl or naphthyl.

The organopolysiloxane can preferably be chosen from polydimethylsiloxanes, polymethylethylsiloxanes, copolymers of dimethylsiloxane and of methylvinylsiloxane, and copolymers of dimethylsiloxane and up to 50 mol % of phenylmethylsiloxane.

Use can advantageously be made of a polydimethylsiloxane.

The organopolysiloxane can be present in the surface composition in an amount which is effective in producing the chased effect (crater formation) and preferably in an amount ranging from 0.0001% to 1.25% by weight with respect to the total weight of the composition, more preferably from 0.001% to 0.5% by weight and better still from 0.001% to 0.25% by weight.

Use may be made, as organopolysiloxane, of those sold in solution in xylene under the name DOW CORNING 61 ADDITIVE by the Company Dow Corning or alternatively those sold under the name RHODORSIL SIL AID 16 by the Company Rhone-Poulenc.

In order to obtain a film exhibiting the chased appearance, the surface composition must comprise at least one metal pigment. Use may be made, as metal pigment, of, for example, an aluminum, copper, zinc, bronze, nickel powders, chromium powder, and equivalent powders.

The metal pigment can be coated, for example, with rosin or fatty acids, such as oleic or linoleic acid.

The metal pigment can have a mean particle size ranging from 5 to 150 $\mu$m, and preferably from 10 to 60 $\mu$m.

Use may be made, as metal pigment, of the aluminum powders sold under the names STAPA LEAFING GRADE, STAPA METTALIC or METALURE L55350 by the Company Eckart, ALUMINUM SUPER 800 by the Company Wolstenholme International, or SILVET ET 1630 by the Company Silberline; or bronze powders sold under the names STAPA GOLDEN BRONZE by the Company Eckart or PASTEL STANDARD by the Company Wolstenholme International.

The metal pigment can be present in the surface composition in a preferred amount ranging from 0.1% to 25% by weight with respect to the total weight of the composition, more preferably from 1% to 10% by weight and better still from 1% to 5% by weight.

The organopolysiloxane and the metal pigment can preferably be present in the surface composition at an organopolysiloxane/metal pigment ratio by weight preferably ranging from 0.1:100 to 5:100, and better still from 0.5:100 to 1.5:100. A film exhibiting a good chased effect can be obtained in this ratio by weight.

According to the invention, the cosmetically acceptable medium of the base composition can comprise an aqueous medium or an organic solvent medium.

In the present application, the term "film-forming polymer" is understood to mean a polymer capable of forming, by itself alone or in the presence of a plasticizing agent, an isolable film. The film-forming polymer of the base composition can be dissolved or dispersed in the form of particles in the cosmetically acceptable medium of the composition.

The film-forming polymer can be chosen in particular from radical polymers, polycondensates and polymers of natural origin, and preferably from the group formed by vinyl polymers, polyurethanes, polyesters, alkyd resins, epoxyester resins, cellulose polymers, such as nitrocellulose or cellulose esters, the resins resulting from the condensation of formaldehyde with an aryisulphonamide, and their mixtures.

The film-forming polymer is preferably dissolved in an organic solvent medium.

The film-forming polymer of the surface composition can preferably comprise at least one cellulose ester. This is because it has been found that the cellulose ester rapidly solidifies the craters formed during the application of the surface composition to the nails and results in a make-up exhibiting a beautiful chased effect.

The cellulose ester used according to the invention can comprise acyl groups, R—CO—, the R group can be chosen from a linear or branched alkyl radical having from 1 to 3 carbon atoms, and their mixtures.

In particular, the cellulose ester can be chosen from cellulose acetate, cellulose acetopropionate and cellulose acetobutyrate, preferably from cellulose acetobutyrate and cellulose acetopropionate, and better still cellulose acetobutyrate.

The cellulose acetobutyrate can preferably comprise a level by weight of acetate group ranging from 1 to 18% and a level by weight of butyrate group ranging from 30 to 60%. Mention may be made, as cellulose acetobutyrate (known as CAB), of those sold under the names CAB-551, CAB-500, CAB-553 or CAB-381 by the Company Eastman Chemical.

The film-forming polymer present in the surface composition can advantageously comprise a mixture of nitrocellulose and cellulose ester as described above.

The nitrocellulose can be chosen from nitrocellulose RS ⅛ sec.; RS ¼ sec.; RS ½ sec; RS 5 sec.; RS 15 sec.; RS 35 sec.; RS 75 sec.; RS 150 sec.; AS ¼ sec.; AS ½ sec.; SS ¼ sec.; SS ½ sec; SS 5 sec., sold in particular by the Company Hercules.

The base and/or surface compositions can preferably comprise from 0.05% to 30% by weight of nitrocellulose and from 0.05 to 30% by weight of cellulose ester, in particular of cellulose acetobutyrate, with respect to the total weight of the composition. The cellulose ester can advantageously be present in the compositions in an amount by weight ranging from 10% to 80% by weight with respect to the total weight of cellulose ester and of nitrocellulose which are present in the composition.

According to an alternative embodiment according to the invention, the base composition can comprise an aqueous medium. The film-forming polymer is generally present in the form of particles in dispersion in the aqueous medium.

Mention may be made, as polymer in aqueous dispersion, of the dispersions of acrylic polymers sold under the names NEOCRYL XK-90®, NEOCRYL A-1070®, NEOCRYL A-1090®, NEOCRYL BT-62®, NEOCRYL A-1079®, or NEOCRYL A-523®, by the Company Zeneca or DOW LATEX 432® by the Company Dow Chemical. It is also possible to employ aqueous dispersions of polyurethane and in particular the polyesterpolyurethanes sold under the names AVALURE UR-405®, AVALURE UR-410®, AVALURE UR-425®, or SANCURE 2060® by the Company Goodrich and the polyetherpolyurethanes sold under the names SANCURE 878® by the Company Goodrich or NEOREZ R 970® by the Company ICI.

The film-forming polymer of the base and surface compositions can be present according to the invention in an amount, on a dry basis, which is effective in producing a film, preferably in an amount ranging from 1% to 60% by weight with respect to the total weight of the composition, and better still from 5% to 45% by weight.

Mention may be made, as organic solvent which can be used in the invention, of:
- ketones, which are liquid at room temperature, such as methyl ethyl ketone, methyl isobutyl ketone, diisobutyl ketone, isophorone, cyclohexanone or acetone;
- alcohols, which are liquid at room temperature, such as ethanol, isopropanol, diacetone alcohol, 2-butoxyethanol or cyclohexanol;
- glycols, which are liquid at room temperature, such as ethylene glycol, propylene glycol, pentylene glycol or glycerol;
- propylene glycol ethers, which are liquid at room temperature, such as propylene glycol monomethyl ether, propylene glycol monomethyl ether acetate or dipropylene glycol mono(n-butyl) ether;
- short-chain esters (having a total of 3 to 8 carbon atoms), such as ethyl acetate, methyl acetate, propyl acetate, n-butyl acetate or isopentyl acetate;
- ethers, which are liquid at room temperature, such as diethyl ether, dimethyl ether or dichlorodiethyl ether;
- alkanes, which are liquid at room temperature, such as decane, heptane, dodecane or cyclohexane;
- cyclic aromatic compounds, which are liquid at room temperature, such as toluene and xylene;
- aldehydes, which are liquid at room temperature, such as benzaldehyde or acetaldehyde; and
- their mixtures.

Use may preferably be made, as organic solvent, of butyl acetate, ethyl acetate, isopropyl alcohol and their mixtures.

In each composition with an organic solvent medium, the organic solvent can be present in an amount ranging from 25 to 95% by weight with respect to the total weight of composition, and preferably from 60% to 80% by weight.

When the base composition according to the invention comprises an aqueous medium, the latter can be comprised of water or alternatively of an aqueous/alcoholic mixture comprising in particular lower ($C_1$–$C_5$) monoalcohols. The amount of water in the composition with an aqueous medium can range from 30 to 95% by weight with respect to the total weight of each composition, and preferably from 60% to 90% by weight.

The pyrogenic silica present in the surface composition can be provided in the form of hydrophilic pyrogenic silica or hydrophobic pyrogenic silica. Use is preferably made of hydrophilic pyrogenic silica.

Pyrogenic silicas can be obtained by high temperature hydrolysis of a volatile silicon compound in an oxyhydrogen flame, producing a finely divided silica. This process makes it possible in particular to obtain hydrophilic silicas which exhibit a large number of silanol groups at their surfaces. Such hydrophilic silicas are sold, for example, under the names AEROSIL 130®, AEROSIL 200®, AEROSIL 255®, AEROSIL 300®, or AEROSIL 380® by the Company Degussa or CAB-O-SIL HS-5®, CAB-O-SIL EH-5®, CAB-O-SIL LM-130®, CAB-O-SIL MS-55®, or CAB-O-SIL M-5®, by the Company Cabot.

It is possible to chemically modify the surface of the silica by a chemical reaction which generates a decrease in the number of silanol groups. It is possible in particular to substitute silanol groups by hydrophobic groups: a hydrophobic silica is then obtained.

The hydrophobic groups can be:
- trimethylsiloxyl groups, which are obtained in particular by treatment of pyrogenic silica in the presence of hexamethyidisilazane. Silicas thus treated are named "Silica silylate" according to the CTFA (6th edition, 1995). They are sold, for example, under the references AEROSIL R812® by the Company Degussa or CAB-O-SIL TS-530® by the Company Cabot.
- dimethylsilyloxy or polydimethylsiloxane group, which are obtained in particular by treatment of pyrogenic silica in the presence of polydimethylsiloxane or of dimethyldichlorosilane. Silicas thus treated are named "Silica dimethyl silylate" according to the CTFA (6th edition, 1995). They are sold, for example, under the references AEROSIL R972® or AEROSIL R974® by the Company Degussa or CAB-O-SIL TS-610® or CAB-O-SIL TS-720® by the Company Cabot.

The pyrogenic silica preferably exhibits a particle size which can be nanometric to micrometric, for example ranging from approximately 5 to 200 nm.

The pyrogenic silica can be present in the surface composition according to the invention in an amount which is effective in producing the chased effect, in particular in an amount ranging from 0.1% to 5% by weight with respect to the total weight of the composition, and preferably from 0.5% to 2% by weight.

It is also possible to introduce a clay, such as organo-modified bentonites, into the surface composition without harming the property of the film.

This clay can be present in an amount ranging from 0.1% to 3% by weight, with respect to the total weight of the composition, and better still from 0.5% to 1.5% by weight, and in a clay/pyrogenic silica ratio by weight ranging up to and including 0.5:1.

Use may be made, as bentonites, of those sold under the names BENTONE 27®, BENTONE 34®, or BENTONE 38® by the Company Rheox or under the name TIXOGEL LG® by the Company Sud Chemie.

An additional agent which is able to form a film can be provided in order to improve the film-forming properties of the composition, in particular of the base composition and/or of the surface composition according to the invention.

Such an additional agent which is able to form a film can be chosen from any compound known to a person skilled in the art as being capable of fulfilling the desired role and can be chosen in particular from plasticizing agents.

In addition, when the base composition according to the invention comprises a film-forming polymer in the form of particles dispersed in an aqueous medium, the additional agent which is able to form a film can also be chosen from coalescence agents.

According to a preferred embodiment of the make-up kit and process according to the invention, the base composition may be capable of forming a film with a different color from that of the chased film obtained with the surface composition. In particular, when the chased film comprises craters exhibiting openings (that is to say, when the tip of the cone of the crater is open), the openings can allow the color of the base layer to appear. A contrast is then observed between the color of the base layer and the color of the chased surface layer. The make-up film then exhibits an original color effect.

The base and surface compositions according to the invention can furthermore comprise adjuvants commonly used in nail varnishes. Mention may be made, among these adjuvants, of thickening agents, spreading agents, wetting agents, dispersing agents, anti-foaming agents, preservatives, UV screening agents, dyes, pigments other than the above-mentioned metal pigments, active principles, surfactants, moisturizing agents, fragrances, neutralizing agents, stabilizing agents and antioxidants.

Of course, a person skilled in the art would take care to choose this or these optional additional compounds and/or the amounts so that the advantageous properties of the composition according to the invention are not, or are not substantially, detrimentally affected by the envisaged addition.

The base composition and the surface composition according to the invention can be prepared by a person skilled in the art on the basis of his general knowledge and according to the state of the art.

The base composition and the surface composition can advantageously be packaged in separate compartments or containers, accompanied by appropriate application means which are identical or different, such as brushes, pens and sponges.

The surface composition can be applied either at one of the ends of the base layer or in the middle or non-continuously, in particular in the form of symmetrical or asymmetrical geometric designs (for example in the form of points, squares, circles or stars), distributed randomly or in an ordered way, with sharp or blurred outlines.

The invention is illustrated in more detail in the following examples.

EXAMPLE 1

A nail varnish was prepared having the following composition:

| | | | |
|---|---|---|---|
| Nitrocellulose | | 15 | g |
| Cellulose acetobutyrate (CAB 381-05 from Eastman Chemical) | | 0.5 | g |
| Alkyd resin | | 9 | g |
| Pyrogenic silica (AEROSIL 200 from Degussa) | | 1 | g |
| Polydimethylsiloxane as a 10% solution in xylene (DOW CORNING 61 ADDITIVE) | | 0.3 | g |
| Aluminium powder coated with rosin SILVET E11630 from Silberline) | | 3 | g |
| Plasticizers | | 6 | g |
| Hectorite | | 0.3 | g |
| Pigment | | 0.2 | g |
| Solvents (ethyl acetate, butyl acetate) | q.s. for | 100 | g |

On application of the varnish to the nails, the instantaneous formation of small craters at the surface of the film, providing a make-up with a chased effect, was observed.

EXAMPLE 2

Two following nail varnish compositions A and B were prepared:

| | | |
|---|---|---|
| Base composition A: | | |
| Nitrocellulose | | 15 g |
| Alkyd resin | | 9 g |
| Plasticizer | | 6 g |
| Hectorite | | 1.5 g |
| Red pigments | | 1.5 g |
| Ethyl acetate, butyl acetate | q.s. for | 100 g |
| Surface composition B: | | |
| Nitrocellulose | | 15 g |
| Cellulose acetobutyrate (CAB 381-05 from Eastman Chemical) | | 0.5 g |
| Alkyd resin | | 9 g |
| Pyrogenic silica (AEROSIL 200 from Degussa) | | 1 g |
| Polydimethylsiloxane as a 10% solution in xylene (DOW CORNING 61 ADDITIVE) | | 0.1 g |
| Aluminium powder coated with rosin (SILVET ET1630 from Silberline) | | 1 g |
| Plasticizers | | 6 g |
| Hectorite | | 0.3 g |
| Pigment | | 0.2 g |
| Solvents (ethyl acetate, butyl acetate) | q.s. for | 100 g |

A base layer of composition A and then, after drying, a surface layer of composition B were applied to the nail. A make-up with a chased effect was obtained. The craters of the surface layer exhibited openings which allowed the red color of the film of the base layer to appear.

The make-up obtained had an overall violet-pink color.

EXAMPLE 3

A nail varnish was prepared having the following composition:

| | | |
|---|---|---|
| Nitrocellulose | | 15 g |
| Cellulose acetopropionate (CAP 482-0.5 from Eastman Chemical) | | 0.5 g |
| Alkyd resin | | 9 g |
| Pyrogenic silica (AEROSIL 200 from Degussa) | | 1 g |
| Polydimethylsiloxane as a 10% solution in xylene (DOW CORNING 61 ADDiTIVE) | | 0.1 g |
| Bronze powder (PASTEL STANDARD from Wolstenholme International) | | 1 g |
| Plasticizers | | 6 g |
| Solvents (ethyl acetate, butyl acetate) | q.s. for | 100 g |

On application of the varnish to the nails, the instantaneous formation of craters on the surface of the film, providing a make-up with a chased effect, was observed.

COMPARATIVE EXAMPLE 4

Outside the Invention

A nail varnish, not forming part of the invention, was prepared having the following composition:

| Nitrocellulose | | 15 g |
| --- | --- | --- |
| Cellulose acetobutyrate (CAB 381 05 from Eastman Chemical) | | 0.5 g |
| Alkyd resin | | 9 g |
| Polydimethylsiloxane as a 10% solution in xylene (DOW CORNING 61 ADDITIVE) | | 0.3 g |
| Aluminium powder coated with rosin (SILVET ET1630 from Silberline) | | 3 g |
| Plasticizers | | 6 g |
| Hectorite | | 1.5 g |
| Pigment | | 0.2 g |
| olvents (ethyl acetate, butyl acetate) | q.s. for | 100 g |

The composition comprised only hectorite as thickening agent.

On application to the nails, it was found that the varnish did not form craters; the film remained smooth and continuous.

What is claimed is:

1. A nail varnish composition comprising, in an organic solvent medium:
    at least one film-forming polymer,
    at least one pyrogenic silica,
    at least one metal pigment, and
    at least one organopolysiloxane having on average from 1.99 to 2.01 hydrocarbonaceous radicals per silicon atom,
    wherein at least 50% of the units of the at least one organopolysiloxane are units of formula RMeSiO in which R is an aliphatic radical having from 1 to 3 carbon atoms, the remaining units of the at least one organopolysiloxane are units of formula $R'_n SiO_{(2-n/2)}$ in which n has a mean value ranging from 1 to 3 and R' is a monovalent hydrocarbonaceous radical,
    wherein a 10% by weight solution of the at least one organopolysiloxane in xylene has a viscosity at 25° C. ranging from 0.0002 $m^2/s$ to 0.01 $m^2/s$, and
    wherein said at least one pyrogenic silica and said at least one film-forming polymer are present in amounts such that the weight ratio of said at least one pyrogenic silica to said at least one film-forming polymer ratio is other than 0.0116:1.

2. The composition according to claim 1, wherein the 10% by weight solution of the at least one organopolysiloxane in xylene has a viscosity ranging from 0.0005 to 0.005 $m^2/s$.

3. The composition according to claim 2, wherein the 10% by weight solution of the at least one organopolysiloxane in xylene has a viscosity ranging from 0.001 $m^2/s$ to 0.0015 $m^2/s$.

4. The composition according to claim 1, wherein R is a methyl radical.

5. The composition according to claim 1, wherein the at least one organopolysiloxane is chosen from polydimethylsiloxanes, polymethylethylsiloxanes, copolymers of dimethylsiloxane and of methylvinylsiloxane, and copolymers of dimethylsiloxane and of phenylmethylsiloxane.

6. The composition according to claim 5, wherein the at least one organopolysiloxane is a polydimethylsiloxane.

7. The composition according to claim 1, wherein the at least one organopolysiloxane is present in the composition in an amount ranging from 0.0001% to 1.25% by weight with respect to the total weight of the composition.

8. The composition according to claim 7, wherein the at least one organopolysiloxane is present in the composition in an amount ranging from 0.001% to 0.5% by weight with respect to the total weight of the composition.

9. The composition according to claim 8, wherein the at least one organopolysiloxane is present in the composition in an amount ranging from 0.001% to 0.25% by weight with respect to the total weight of the composition.

10. The composition according to claim 1, wherein the at least one film-forming polymer is chosen from radical polymers, polycondensates and polymers of natural origin.

11. The composition according to claim 1, wherein the at least one film-forming polymer is chosen from vinyl polymers, polyurethanes, polyesters and cellulose polymers.

12. The composition according to claim 1, wherein the at least one film-forming polymer is present in the composition in an amount ranging from 1% to 60% by weight with respect to the total weight of the composition.

13. The composition according to claim 12, wherein the at least one film-forming polymer is present in the composition in an amount ranging from 5% to 45% by weight with respect to the total weight of the composition.

14. The composition according to claim 1, wherein the at least one film-forming polymer comprises at least one cellulose ester.

15. The composition according to claim 14, wherein the at least one film-forming polymer comprises at least one cellulose ester chosen from cellulose acetobutyrate and cellulose acetopropionate.

16. The composition according to claim 14, wherein the cellulose ester is present in the composition in an amount ranging from 0.5% to 30% by weight with respect to the total weight of the composition.

17. The composition according to claim 1, wherein the at least one film-forming polymer comprises at least one nitrocellulose.

18. The composition according to claim 17, wherein the at least one nitrocellulose is present in the composition in an amount ranging from 0.5% to 30% by weight with respect to the total weight of the composition.

19. The composition according to claim 1, wherein the at least one metal pigment is chosen from aluminum powder, copper powder, zinc powder, bronze powder, nickel powder, and chromium powder.

20. The composition according to claim 1, wherein the at least one metal pigment is present in the composition in an amount ranging from 0.1% to 25% by weight with respect to the total weight of the composition.

21. The composition according to claim 20, wherein the at least one metal pigment is present in the composition in an amount ranging from 1% to 10% by weight with respect to the total weight of the composition.

22. The composition according to claim 1, wherein the at least one organopolysiloxane and the at least one metal pigment are present in the composition in an organopolysiloxane/metal pigment ratio by weight ranging from 0.1:100 to 5:100.

23. The composition according to claim 22, wherein the at least one organopolysiloxane and the at least one metal pigment are present in the composition in an organopolysiloxane/metal pigment ratio by weight ranging from 0.5:100 to 1.5:100.

24. The composition according to claim 1, wherein the at least one pyrogenic silica is at least one hydrophilic silica.

25. The composition according to claim 1, wherein the at least one pyrogenic silica is present in the composition in an amount ranging from 0.1% to 5% by weight with respect to the total weight of the composition.

26. The composition according to claim 25, wherein the at least one pyrogenic silica is present in the composition in an amount ranging from 0.5% to 2% by weight with respect to the total weight of the composition.

27. The composition according to claim 1, wherein the composition additionally comprises at least one clay, wherein the at least one clay is present in the composition in an amount so that the clay/pyrogenic silica ratio by weight is not greater than 0.5:1.

28. The composition according to claim 1, wherein the composition comprises at least one additive chosen from thickening agents, spreading agents, wetting agents, dispersing agents, anti-foaming agents, preservatives, UV screening agents, dyes, pigments other than the at least one metal pigment, active principles, surfactants, moisturizing agents, fragrances, neutralizing agents, stabilizing agents, and antioxidants.

29. A cosmetic process for making up nails, comprising applying to nails a composition comprising, in an organic solvent medium:
   at least one film-forming polymer,
   at least one pyrogenic silica,
   at least one metal pigment, and
   at least one organopolysiloxane having on average from 1.99 to 2.01 hydrocarbonaceous radicals per silicon atom,
   wherein at least 50% of the units of the at least one organopolysiloxane are units of formula RMeSiO in which R is an aliphatic radical having from 1 to 3 carbon atoms, the remaining units of the at least one organopolysiloxane are units of formula $R'_n SiO_{(2-n/2)}$ in which n has a mean value ranging from 1 to 3 and R' is a monovalent hydrocarbonaceous radical,
   wherein a 10% by weight solution of the at least one organopolysiloxane in xylene has a viscosity at 25° C. ranging from 0.0002 $m^2$/s to 0.01 $m^2$/s, and
   wherein said at least one pyrogenic silica and said at least one film-forming polymer are present in amounts such that the weight ratio of said at least one pyrogenic silica to said at least one film-forming polymer ratio is other than 0.0116:1.

30. A cosmetic process for making up nails, comprising applying to nails:
   a first layer of a first composition comprising, in a cosmetically acceptable medium, at least one first film-forming polymer,
   and then applying to at least a portion of the first layer a second layer of a second composition comprising at least one second film-forming polymer in an organic solvent medium, at least one pyrogenic silica, at least one metal pigment and at least one organopolysiloxane having on average from 1.99 to 2.01 hydrocarbonaceous radicals per silicon atom, wherein at least 50% of the units of the organopolysiloxane are units of formula RMeSiO in which R is an aliphatic radical having from 1 to 3 carbon atoms, the remaining units of the at least one organopolysiloxane are units of formula $R'_n SiO_{(2-n/2)}$ in which n has a mean value ranging from 1 to 3 and R' is a monovalent hydrocarbonaceous radical, wherein a 10% by weight solution of the at least one organopolysiloxane in xylene has a viscosity at 25° C. ranging from 0.0002 to 0.01 $m^2$/s,
   wherein the first composition does not comprise an organopolysiloxane that is the same as the at least one organopolysiloxane in the second composition.

31. The process according to claim 30, wherein the 10% by weight solution of the at least one organopolysiloxane in xylene has a viscosity ranging from 0.0005 to 0.005 $m^2$/s.

32. The process according to claim 31, wherein the 10% by weight solution of the at least one organopolysiloxane in xylene has a viscosity ranging from 0.001 $m^2$/s to 0.0015 $m^2$/s.

33. The process according to claim 30, wherein R is a methyl radical.

34. The process according to claim 30, wherein the at least one organopolysiloxane is a polydimethylsiloxane.

35. The process according to claim 30, wherein the at least one organopolysiloxane is present in the second composition in an amount ranging from 0.0001% to 1.25% by weight with respect to the total weight of the second composition.

36. The process according to claim 35, wherein the at least one organopolysiloxane is present in the second composition in an amount ranging from 0.001% to 0.5% by weight with respect to the total weight of the second composition.

37. The process according to claim 36, wherein the at least one organopolysiloxane is present in the second composition in an amount ranging from 0.001% to 0.25% by weight with respect to the total weight of the second composition.

38. The process according to claim 30, wherein the at least one metal pigment is chosen from aluminum powder, copper powder, zinc powder, bronze powder, nickel powder, and chromium powder.

39. The process according to claim 30, wherein the at least one metal pigment is present in the second composition in an amount ranging from 0.1% to 25% by weight with respect to the total weight of the second composition.

40. The process according to claim 39, wherein the at least one metal pigment is present in the second composition in an amount ranging from 1% to 10% by weight with respect to the total weight of the second composition.

41. The process according to claim 30, wherein the at least one organopolysiloxane and the at least one metal pigment are present in the second composition in an organopolysiloxane/metal pigment ratio by weight ranging from 0.1:100 to 5:100.

42. The process according to claim 41, wherein the at least one organopolysiloxane and the at least one metal pigment are present in the second composition in an organopolysiloxane/metal pigment ratio by weight ranging from 0.5:100 to 1.5:100.

43. The process according to claim 30, wherein the at least one pyrogenic silica comprises at least one hydrophilic silica.

44. The process according to claim 43, wherein the at least one pyrogenic silica is present in the second composition in an amount ranging from 0.1% to 5% by weight with respect to the total weight of the second composition.

45. The process according to claim 44, wherein the at least one pyrogenic silica is present in the second composition in an amount ranging from 0.5% to 2% by weight with respect to the total weight of the second composition.

46. The process according to claim 30, wherein the first composition comprises an organic solvent medium or an aqueous medium.

47. The process according to claim 30, wherein the at least one first and second film-forming polymers are independently chosen from radical polymers, polycondensates and polymers of natural origin.

48. The process according to claim 47, wherein the at least one first and second film-forming polymers are independently chosen from vinyl polymers, polyurethanes, polyesters and cellulose polymers.

49. The process according to claim 30, wherein the at least one first film-forming polymer is present in the first composition in an amount ranging from 1% to 60% by weight with respect to the total weight of the first composition.

50. The process according to claim 49, wherein the at least one first film-forming polymer is present in the first composition in an amount ranging from 5% to 45% by weight with respect to the total weight of the first composition.

51. The process according to claim 30, wherein the at least one second film-forming polymer is present in the second composition in an amount ranging from 1% to 60% by weight with respect to the total weight of the second composition.

52. The process according to claim 51, wherein the at least one second film-forming polymer is present in the second composition in an amount ranging from 5% to 45% by weight with respect to the total weight of the second composition.

53. The process according to claim 30, wherein the at least one second film-forming polymer comprises at least one cellulose ester.

54. The process according to claim 30, wherein the at least one second film-forming polymer comprises at least one cellulose ester chosen from cellulose acetobutyrate and cellulose acetopropionate.

55. The process according to claim 53, wherein the at least one cellulose ester is present in the second composition in an amount ranging from 0.5% to 30% by weight with respect to the total weight of the second composition.

56. The process according to claim 30, wherein the at least one second film-forming polymer comprises at least one nitrocellulose.

57. The process according to claim 56, wherein the at least one nitrocellulose is present in the second composition in an amount ranging from 0.5% to 30% by weight with respect to the total weight of the second composition.

58. A make-up kit comprising a first compartment and a second compartment, wherein the first compartment comprises:
 a first composition comprising at least one first film-forming polymer in a cosmetically acceptable medium, and wherein the second compartment comprises:
 a second composition comprising at least one second film-forming polymer in an organic solvent medium, at least one pyrogenic silica, at least one metal pigment and at least one organopolysiloxane having on average from 1.99 to 2.01 hydrocarbonaceous radicals per silicon atom, wherein at least 50% of the units of the at least one organopolysiloxane are units of formula RMeSiO in which R is an aliphatic radical having from 1 to 3 carbon atoms, the other remaining units of the at least one organopolysiloxane are units of formula $R'_n SiO_{(2-n/2)}$ in which n has a mean value ranging from 1 to 3 and R' is a monovalent hydrocarbonaceous radical, wherein a 10% by weight solution of the at least one organopolysiloxane in xylene has a viscosity at 25° C. ranging from 0.0002 m$^2$/s to 0.01 m$^2$/s,
 wherein the first composition does not comprise an organopolysiloxane that is the same as the at least one organopolysiloxane in the second composition.

59. The kit according to claim 58, wherein the 10% by weight solution of the at least one organopolysiloxane in xylene has a viscosity ranging from 0.0005 to 0.005 m$^2$/s.

60. The kit according to claim 59, wherein the 10% by weight solution of the at least one organopolysiloxane in xylene has a viscosity ranging from 0.001 m$^2$/s to 0.0015 m$^2$/s.

61. The kit according to claim 58, wherein R is a methyl radical.

62. The kit according to claim 58, wherein the at least one organopolysiloxane in the second composition is a polydimethylsiloxane.

63. The kit according to claim 58, wherein the at least one organopolysiloxane is present in the second composition in an amount ranging from 0.0001% to 1.25% by weight with respect to the total weight of the second composition.

64. The kit according to claim 63, wherein the at least one organopolysiloxane is present in the second composition in an amount ranging from 0.001% to 0.5% by weight with respect to the total weight of the second composition.

65. The kit according to claim 64, wherein the at least one organopolysiloxane is present in the second composition in an amount ranging from 0.001% to 0.25% by weight with respect to the total weight of the second composition.

66. The kit according to claim 58, wherein the at least one metal pigment is chosen from aluminum powder, copper powder, zinc powder, bronze powder, nickel powder, and chromium powder.

67. The kit according to claim 58, wherein the at least one metal pigment is present in the second composition in an amount ranging from 0.1% to 25% by weight with respect to the total weight of the second composition.

68. The kit according to claim 67, wherein the at least one metal pigment is present in the second composition in an amount ranging from 1% to 10% by weight with respect to the total weight of the second composition.

69. The kit according to claim 58, wherein the at least one organopolysiloxane and the at least one metal pigment are present in the second composition in an organopolysiloxane/metal pigment ratio by weight ranging from 0.1:100 to 5:100.

70. The kit according to claim 69, wherein the at least one organopolysiloxane and the at least one metal pigment are present in the second composition in an organopolysiloxane/metal pigment ratio by weight ranging from 0.5:100 to 1.5:100.

71. The kit according to claim 58, wherein the at least one pryogenic silica is at least one hydrophilic pyrogenic silica.

72. The kit according to claim 58, wherein the at least one pyrogenic silica is present in the second composition in an amount ranging from 0.1% to 5% by weight with respect to the total weight of the second composition.

73. The kit according to claim 72, wherein the at least one pyrogenic silica is present in the second composition in an amount ranging from 0.5% to 2% by weight with respect to the total weight of the second composition.

74. The kit according to claim 58, wherein the first composition comprises an organic solvent medium or an aqueous medium.

75. The kit according to claim 58, wherein the at least one first and second film-forming polymers are independently chosen from radical polymers, polycondensates and polymers of natural origin.

76. The kit according to claim 75, wherein the first and second film-forming polymers are independently chosen from vinyl polymers, polyurethanes, polyesters and cellulose polymers.

77. The kit according to claim 58, wherein the at least one first film-forming polymer is present in the first composition in an amount ranging from 1% to 60% by weight with respect to the total weight of the first composition.

78. The kit according to claim 77, wherein the at least one first film-forming polymer is present in the first composition in an amount ranging from 5% to 45% by weight with respect to the total weight of the first composition.

79. The kit according to claim 58, wherein the at least one second film-forming polymer is present in the second composition in an amount ranging from 1% to 60% by weight with respect to the total weight of the second composition.

80. The kit according to claim 79, wherein the at least one second film-forming polymer is present in the second composition in an amount ranging from 5% to 45% by weight with respect to the total weight of the second composition.

81. The kit according to claim 58, wherein the at least one second film-forming polymer comprises at least one cellulose ester.

82. The kit according to claim 81, wherein the at least one second film-forming polymer comprises at least one cellulose ester chosen from cellulose acetobutyrate and cellulose acetopropionate.

83. The kit according to claim 81, wherein the at least one cellulose ester is present in the second composition in an amount ranging from 0.5% to 30% by weight with respect to the total weight of the second composition.

84. The kit according to claim 58, wherein the at least one second film-forming polymer comprises at least one nitrocellulose.

85. The kit according to claim 84, wherein the at least one nitrocellulose is present in the second composition in an amount ranging from 0.5% to 30% by weight with respect to the total weight of the second composition.

86. Made-up false nails comprising false nails containing:

a first layer of a first composition comprising, in a cosmetically acceptable medium, at least one first film-forming polymer, and a second layer covering at least a portion of the first layer, said second composition comprising at least one second film-forming polymer in an organic solvent medium, at least one pyrogenic silica, at least one metal pigment and at least one organopolysiloxane having on average from 1.99 to 2.01 hydrocarbonaceous radicals per silicon atom, wherein at least 50% of the units of the organopolysiloxane being units of formula RMeSiO in which R is an aliphatic radical having from 1 to 3 carbon atoms, the remaining units of the at least one organopolysiloxane are units of formula $R'_n SiO_{(2-n/2)}$ in which n has a mean value ranging from 1 to 3 and R' is a monovalent hydrocarbonaceous radical, wherein a 10% by weight solution of the at least one organopolysiloxane in xylene has a viscosity at 25° C. ranging from 0.0002 to 0.01 $m^2$/s, wherein the first composition does not comprise an organopolysiloxane that is the same as the at least one organopolysiloxane in the second composition.

* * * * *